United States Patent
Karlsson et al.

(10) Patent No.: US 9,095,377 B2
(45) Date of Patent: Aug. 4, 2015

(54) DISTRACTION DEVICE

(75) Inventors: Per-Olof Karlsson, Alingsas (SE); Ulf Johansson, Onsala (SE)

(73) Assignee: Nobel Biocare Services AG, Zurich-Flughafen (CH)

( * ) Notice: Subject to any disclaimer, the term of this patent is extended or adjusted under 35 U.S.C. 154(b) by 552 days.

(21) Appl. No.: 12/738,281

(22) PCT Filed: Oct. 22, 2008

(86) PCT No.: PCT/EP2008/008917
§ 371 (c)(1),
(2), (4) Date: May 20, 2010

(87) PCT Pub. No.: WO2009/053037
PCT Pub. Date: Apr. 30, 2009

(65) Prior Publication Data
US 2010/0312248 A1    Dec. 9, 2010

(51) Int. Cl.
*A61B 17/68* (2006.01)
*A61C 8/02* (2006.01)
*A61B 17/66* (2006.01)

(52) U.S. Cl.
CPC ............. *A61B 17/68* (2013.01); *A61B 17/663* (2013.01); *A61B 17/666* (2013.01); *A61C 8/0006* (2013.01)

(58) Field of Classification Search
USPC ............ 606/60, 90, 320; 433/6, 7, 12, 18, 19; 623/17.11; 411/412, 413
See application file for complete search history.

(56) References Cited

U.S. PATENT DOCUMENTS

| | | | |
|---|---|---|---|
| 1,202,799 A * | 10/1916 | Canning | .......................... 433/12 |
| 3,709,219 A * | 1/1973 | Halloran | ....................... 606/105 |
| 5,766,173 A | 6/1998 | Ross, Jr. et al. | |
| 5,820,369 A | 10/1998 | Kvarnstrom et al. | |
| 6,306,143 B1 | 10/2001 | Kvarnstrom et al. | |
| 6,652,535 B2 | 11/2003 | Kvarnstrom et al. | |
| 6,964,566 B2 | 11/2005 | Sapian | |
| 2002/0156485 A1 | 10/2002 | Sellers et al. | |
| 2004/0176769 A1 | 9/2004 | Furutani et al. | |
| 2010/0332248 A1 | 12/2010 | Pettersson | |

FOREIGN PATENT DOCUMENTS

| | | |
|---|---|---|
| DE | 200 04 588 | 7/2001 |
| WO | WO 02/28298 | 4/2002 |
| WO | WO 03/073955 | 9/2003 |
| WO | WO 2005/009260 | 2/2005 |

(Continued)

OTHER PUBLICATIONS

International Search Report in corresponding European Application No. PCT/EP2008/008917, Dated Apr. 7, 2009, 4 pages.

(Continued)

*Primary Examiner* — Christian Sevilla
(74) *Attorney, Agent, or Firm* — Knobbe, Martens, Olson & Bear, LLP

(57) ABSTRACT

A device, kit, and method are provided for distracting bone. The device can comprise a bar and at least one connection interface. For example, the bar can comprise a first connection interface configured for releasable connection of the bar to at least one fixture inserted in a bone portion to be distracted. A second connection interface can be configured to connect the bar to a level adjustment device for distracting the bone portion.

15 Claims, 10 Drawing Sheets

(56) References Cited

FOREIGN PATENT DOCUMENTS

| | | |
|---|---|---|
| WO | WO 2006/108160 | 10/2006 |
| WO | WO 2006/137045 | 12/2006 |

OTHER PUBLICATIONS

Meehan, et al. "Virtual 3D Planning and Guidance of Mandibular Distraction Osteogenesis". Computer Aided Surgery, 2006.

* cited by examiner

DISTRACTION DEVICE

PRIORITY INFORMATION

This application is a U.S. National Phase of International Application No. PCT/EP2008/008917, filed Oct. 22, 2008, which claims priority to Swedish Patent Application No. SE 702385-6, filed Oct. 25, 2007, each of which is hereby incorporated by reference in its entirety.

BACKGROUND

1. Field of the Inventions

The present inventions pertain in general to the field of distraction of bone. More particularly, some embodiments of the inventions relate to a device for use in distracting bone, a kit of components for forming a device for distracting bone and a method for forming a device for distracting bone.

2. Background of the Inventions

Distraction of bone can be used in situations wherein it is desired to remodel, for example, an existing shape or contour of bone into a desired shape. This is for example used in dental applications to remodel the ridge of the jawbone of a patient. The patient may have a lost a portion of the ridge in an accident, during a surgical procedure, etc. Also, the ridge may be resorbed if the patient has been edentulous for a long period of time.

In some applications when bone distraction is employed, it is important that the end-location of the bone can be well defined, preferably prior to starting the surgical procedure. For example, when remodeling at least a portion of a ridge, the ultimate object is often to also restore one or several teeth. For a partial restoration, it is desired that a restored portion of the ridge aligns with an existing portion of the ridge, such that a desired ridge line is obtained. The same applies for restoring the ridge of a fully edentulous patient, i.a. that a desired contour is obtained. For the partial restoration, it is desired to be able to install a dental restoration, such as a bridge or crown, which conforms to existing teeth, for example by having approximately the same length as the existing teeth. For the fully edentulous case, the same considerations apply to provide desired esthetics, e.g. a naturally looking denture. Hence, distracting bone in a well-defined manner, such that the bone distracted ends up as desired or planned, provides for a desired or planned bone and/or soft tissue contour as well as desired esthetics. This is for example useful for dental restorative purposes.

Hence, an improved device for distracting bone would be advantageous, in particular allowing for increased flexibility, cost-effectiveness, reliability, patient safety, predictability of surgery, and/or patient satisfaction would be advantageous.

SUMMARY

Accordingly, some embodiments of the present inventions preferably seeks to mitigate, alleviate or eliminate one or more deficiencies, disadvantages or issues in the art, such as the above-identified, singly or in any combination by providing a device, a kit of components, and a method according to the appended patent claims.

According to a first aspect of some embodiments, a device for use in distracting bone comprises a bar, which comprises a first connection interface configured for releasable connection of the bar to at least one fixture inserted in a bone portion to be distracted. The bar also comprises a second connection interface configured to connect the bar to a level adjustment device for distracting the bone portion.

The second connection interface may comprise a first engagement part and a second engagement part, which are configured to releasably connect the level adjustment device to the bar. A longitudinal axis of the first engagement part may be arranged substantially parallel to a longitudinal axis of the second engagement part.

Each of the first and the second engagement part may comprise a threaded recess of the bar.

The device may comprise the level adjustment device. The level adjustment device may comprise a support, which may comprise an adjustment interface and an intermediate member, such as a rod. The intermediate member may be displaceably connected to the adjustment interface and displaceable in its a axial direction.

The adjustment interface may comprise a seat, and a swivel device, which may be rotatably arranged in the seat. The intermediate member may displaceably connected to the swivel device.

The intermediate member may be a rod comprising at least one threaded section located along the length of the rod. The threaded section may be configured to engage a threaded through bore of the swivel device.

The rod may comprise a plurality of spaced threaded sections.

The swivel device may comprise at least one flange. The seat may comprise at least one recess. An exterior surface of the swivel device may be at least partly complementary in shape to the shape of an interior surface of the recess of the seat.

The swivel device may comprise a first portion having a first diameter, and a second portion having a second diameter, which is larger than the first diameter.

The first and the second portions of the swivel device may be cylindrical.

The swivel device may comprise at least one groove configured to mate with a tool for rotating the swivel device. A plane of the groove may extend substantially perpendicularly, or substantially in parallel, to the longitudinal axis of the intermediate member.

According to a second aspect of some embodiments, a kit of components for forming a distraction device comprises an intermediate member having a first and a second end, a first locator for positioning the first end of the intermediate member within a bar of a distraction device, a second locator for positioning a seat of a support of the distraction device, and a swivel device configured to be rotatably received in the seat and to position the second end of the intermediate member within the support.

The first and the second end of the intermediate member may be threaded. Each of the first and the second locator may comprise a threaded recess for threadadly engaging the intermediate member.

The second locator may comprise a first portion with a first diameter and a second portion with a second diameter, which is larger than the first diameter.

The second locator may comprise a third portion having a third diameter, which is smaller than the first diameter of the second locator. The third portion may comprise a threaded through bore for threadadly engaging the intermediate portion.

The shape of an exterior surface of the swivel device may be at least complementary to the shape of an interior surface of the seat.

According to a further aspect of some embodiments of the inventions, a method for forming a distraction device comprises providing an intermediate member having a first and a second end, providing a first locator connecting the first end to the first locator, positioning the first locator within a bar of a distraction device, providing a second locator, connecting the second end to the second locator, forming a bar around the first locator, and forming a support around the second locator. The second locator provides a seat for a swivel device, which is configured to be rotatably received in the seat.

The method may comprise releasing the first end of the intermediate member from the first locator, connecting a third locator to the first locator, and scanning at least a portion of the exterior surface of at least one of the third locator and the bar.

The method may comprise arranging the first locator in parallel with the second locator within the bar.

Further embodiments of the inventions are defined in the dependent claims, wherein features for the second and subsequent aspects of the inventions are as for the first aspect mutatis mutandis.

Some embodiments of the inventions provide for predictability of a bone distraction procedure.

Some embodiments of the inventions provide for a full or partial restoration of a ridge of a jawbone of a patient.

Some embodiments of the inventions provide for restoration of a ridge of a jawbone of a patient in combination with providing at least one dental fixture for supporting a dental prosthesis in the restored portion of the ridge.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the inventions are capable of will be apparent and elucidated from the following description of embodiments of the present inventions, reference being made to the accompanying drawings, in which

FIG. 3b is a top view of the swivel device of FIG. 3a;

FIG. 6b is a top view of the locator of FIG. 6a;

DESCRIPTION OF THE EMBODIMENTS

Figure 1:
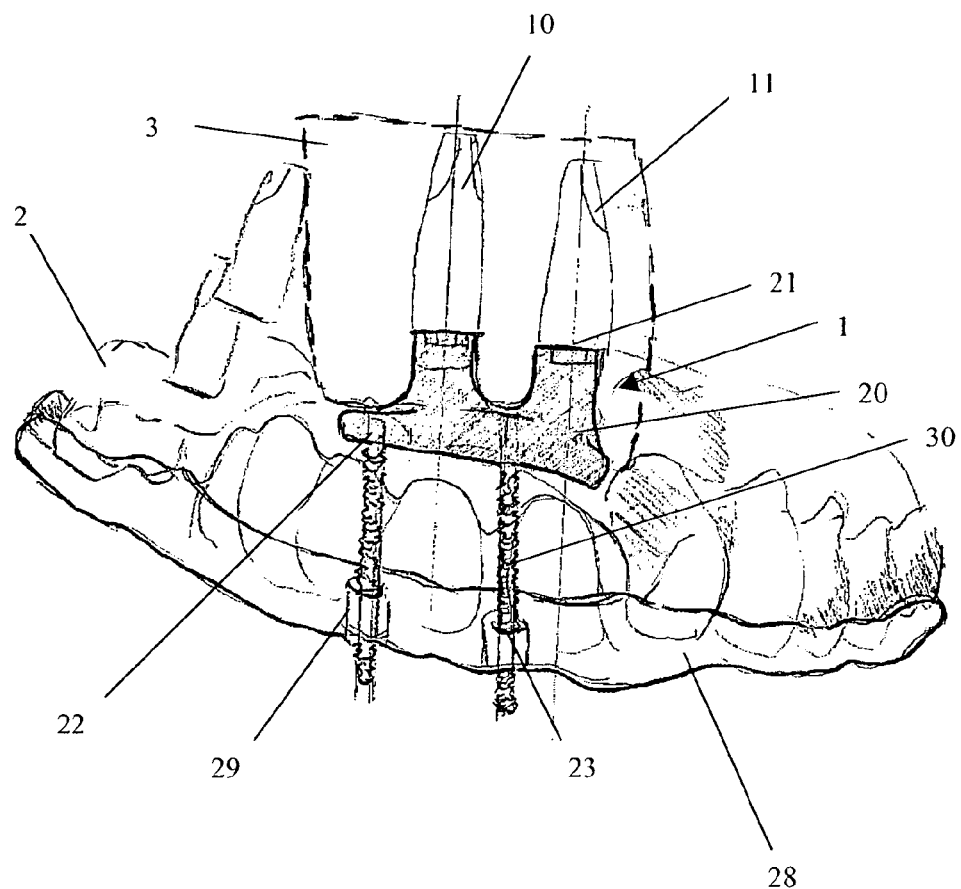
FIG. 1 is a schematic view of the device for distracting bone connected to fixtures and teeth of a patient, according to an embodiment.

Specific embodiments of the inventions now will be described with reference to the accompanying drawings. These inventions may, however, be embodied in many different forms and should not be construed as limited to the embodiments set forth herein; rather, these embodiments are provided so that this disclosure will be thorough and complete, and will fully convey the scope of the inventions to those skilled in the art. The terminology used in the detailed description of the embodiments illustrated in the accompanying drawings is not intended to be limiting of the inventions. In the drawings, like numbers refer to like elements.

FIG. 1 illustrates an embodiment of a device 1 for use in distracting bone. In the following, remodeling the ridge of a jawbone 2 of a partially edentulous patient will be described in relation to various embodiments of the device 1. The inventions are not limited to use in remodeling of the ridge, but can be used in other applications, such as maxillofacial and/or craniofacial applications.

The device 1 according to the inventions is devised for use together with at least one fixture 10, 11. The fixture may e.g. be a dental fixture. The dental fixture may be a screw type fixture having threads devised for screwing the fixture 10, 11 into the bone. Alternatively, the fixture 10, 11 is non-threaded, such as a press-fit fixture. According to embodiments of the inventions, the fixture 10, 11 will first be attached to a bone portion 3 to be distracted. The fixture 10, 11 can be left to osseointegrate with the bone portion 3 before distraction is commenced, such as for 2-6 months. Then, the device 1 is attached to the fixture 10, 11. Consequently, the bone portion 3 can be distracted or moved using the device 1 by applying a force to the fixture 10, 11. The fixture provides for anchoring of the device 1 to the bone portion 3.

The device 1 comprises a bar 20. The bar 20 comprises a first connection interface 21 and a second connection interface 22. The first connection interface is configured for releasable connection of the bar 20 to the fixture 10, 11 inserted into the bone portion 3 to be distracted. Hence, the bar 20 can be attached to the fixture 10, 11 after the healing period and detached after the distraction procedure. The second connection interface 22 is configured to connect the bar 20 to a level adjustment device 23. The level adjustment device 23 is configured to distract the bone portion 3.

The shape of a surface the first connection interface 21 is at least partly complementary to the shape of a surface of a connection interface of the fixture 10, 11. The connection interface of the fixture 10, 11 may e.g. be a hexagonal protrusion with a threaded recess, such as used for the Brånemark System® available from the applicant of the present application. Thus, the first connection interface 21 may be a hexagonal recess with a through bore for receiving a screw. Alternatively, the connection interface of the fixture 10, 11 is a cylindrical recess with a plurality of semi-circular lobes, such as used in the Replace® system available from the applicant of the present application. Hence, the first connection interface 21 may be a cylindrical protrusion with a plurality of semi-circular protrusions. Another possibility is that the first connection interface 21 is a protrusion shaped as a truncated cone with a hexagonally shaped end. The semi-circular protrusion/recess and the hexagonal shape forms an anti-rotational locking of the bar 20 relative the fixture 10, 11. Hence, an engaging connection is formed between the bar 20 and the fixture 10, 11. However, in other embodiments, a non-engaging connection between the bar 20 and the fixture 10, 11 is provided. In the non-engaging connection, the bar does not engage the semi-circular protrusion/recess or the hexagonal shape of the fixture 10, 11.

For connecting the bar 20 to the fixture 10, 11, the bar may comprise a though bore having a seat. A screw may pass through the through bar and a thread of the screw may attach a thread of the connection interface of the fixture 10, 11. A head of the screw may abut the seat of the through bore of the bar 20 when the screw is fully seated.

Figure 2:
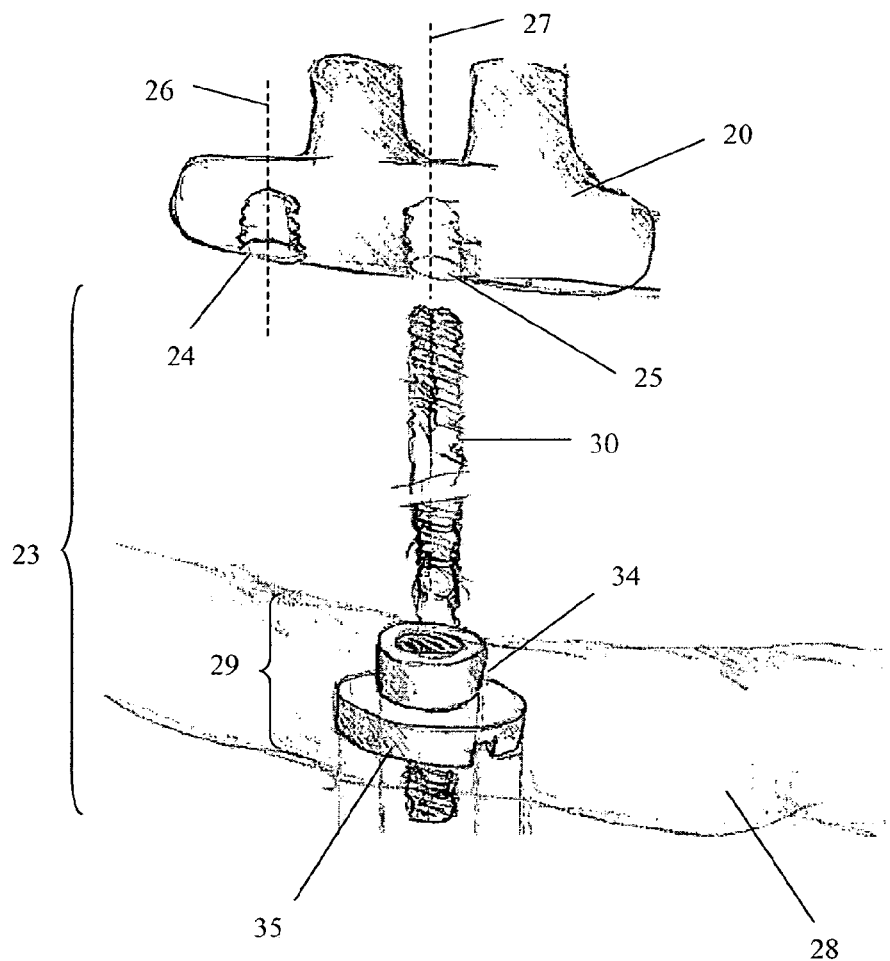
FIG. 2 is a schematic view of the device for distracting bone, according to an embodiment.

FIG. 2 illustrates one embodiment of the bar 20 and the level adjustment device 23. In this embodiment, the second connection interface 22 comprises a first engagement part 24 and a second engagement part 25. The first engagement part 24 and the second engagement part 25 are configured to releasably connect the level adjustment device 23 to the bar 20. In this embodiment, the first engagement part 25 and the second engagement part 25 each comprises a threaded recess of the bar. The depth of the threaded recess may be in the range of 2.5-4 mm, preferably around 2 mm. The diameter of the threaded recess may be in the range of 1.5-2 mm, preferably 1.7-1.75 mm. In other embodiments, the engagement part comprises a bayonet fitting.

The inventions may in some embodiments provide for individual positioning of one or several fixtures 10, 11 without taking into account the final location of the bone portion 3. Instead, the optimal location for each fixture 10, 11 can be chosen. Then, the final position of the bone portion 3 is controlled by means of the device 1. The position of the first connection interface 21 and the second connection interface 22 in the bar 3, as well as the shape of the bar provides the final location of the bone portion 3. Hence, distraction of the bone portion 3 to a predefined location is provided for, wherein predictable bone distraction is provided. As the locations of each fixture 10, 11 can be determined independently of any other fixture, the device 1 is very flexible.

In some embodiments, a longitudinal axis 26 of the first engagement part 24 is substantially parallel to a longitudinal axis 27 of the second engagement part 27. This provides for displacing the bar 20 in a desired direction without causing any strain on the bar. This would not be possible if the adjustment device 23 is connected directly to non-parallel fixtures 10, 11.

FIGS. 1 and 2 illustrate two embodiments of the adjustment device 23, which can be provided together with the bar 20 or as a separate component. In the embodiment of FIG. 1, the level adjustment device 23 comprises a support 28. In these embodiments, the level adjustment device 23 comprises an adjustment interface 29 and an intermediate member 30. The intermediate member 30 is displaceably connected to the adjustment interface 29. Furthermore, the intermediate member 30 is displaceable in its axial direction. Hence, when the intermediate member 30 is connected to the bar 20 and displaced, the bar 20 and the bone portion 3 will be displaced in the axial direction of the intermediate member 30 and relative the support 28. Hence, the direction of the displacement of the bone portion 3 can be controlled by controlling the axial location of the intermediate member 30. The adjustment interface 20 can be used to displace the intermediate member 30.

Figure 3A:
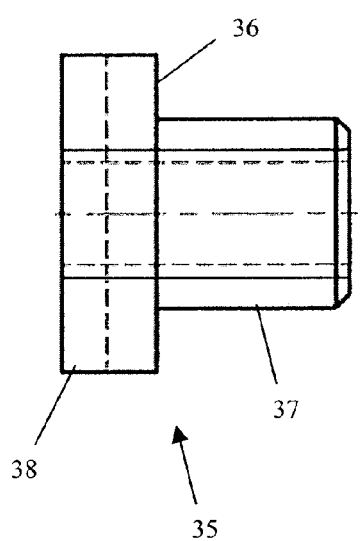
FIG. 3a is a cross-sectional view of a swivel device, according to an embodiment.

The intermediate member 30 may comprise at least one rod 31, 32. In the embodiment of FIG. 3, the intermediate member comprises a first rod 31 and a second rod 32.

In the embodiment of FIG. 1, the adjustment interface 29 comprises a threaded through bore 33 of the support 28 and a tool engagement section (not shown) at a free and of the rod 31, 32. The rod 31, 32 comprises a threaded section engaging the threaded through bore 33 of the support. By rotating the rod 31, 32, it will be displaced relatively the support 28. Hence, the position of the intermediate member 30 and the bone portion 3, which has a fixed relationship relative the intermediate portion 30 and the bar 20, relative the support 28 is adjusted.

In the embodiment of FIG. 2, the adjustment interface 29 comprises a seat 34, and a swivel device 35, which is rotatably arranged in the seat. The intermediate member 30 is displaceably connected to the swivel device 35.

FIG. 3 illustrates the swivel device 35, which comprises at least one flange 36. The seat 34 comprises at least one recess (not shown). An exterior surface of the swivel device is at least partly complementary in shape to the shape of an interior surface of the recess of the seat 34. The swivel device 35 comprises a first portion 37 having a first diameter, and a second portion 38 having a second diameter, which is larger than the first diameter. The first diameter may be in the range of 2.5-3.5 mm, preferably about 2.95 mm. The thickness of the first portion 37 may be in the range of 2.5-3.5 mm, preferably about 3 mm. The thickness of the second portion 38 may be in the range of 1-3 mm, preferably about 1.5 mm.

Is some embodiments, such as in the embodiment of FIG. 3, the first and the second portions 37, 38 of the swivel device 37, 38 are cylindrical. In other embodiments, the first and second portions 37, 38 of the swivel device 35 are flaring towards the free end of the first portion 37.

The swivel device 35 comprises a threaded through bore 39. The thread of the threaded through bore 29 mates with a thread of the rod 31, 32.

Figure 3B:
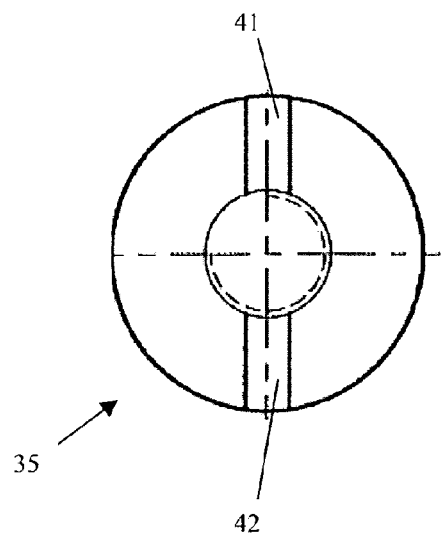

FIG. 3b illustrates a top portion 40 of the swivel device 35. The top portion 40 of the swivel device 35 comprises at least one groove or slot 41, 42 configured to mate with a tool 60 (FIGS. 10-10b) for rotating the swivel device 35. In the embodiment of FIG. 3b, the swivel device 35 comprises a first and a second groove 41, 42. A plane of the groove 41, 42 extends substantially perpendicularly to the longitudinal axis of the intermediate member 30. In other embodiments, a plurality of grooves forms a star configuration (not shown). The grooves may extend substantially in parallel to the longitudinal axis of the intermediate member.

Figure 4:
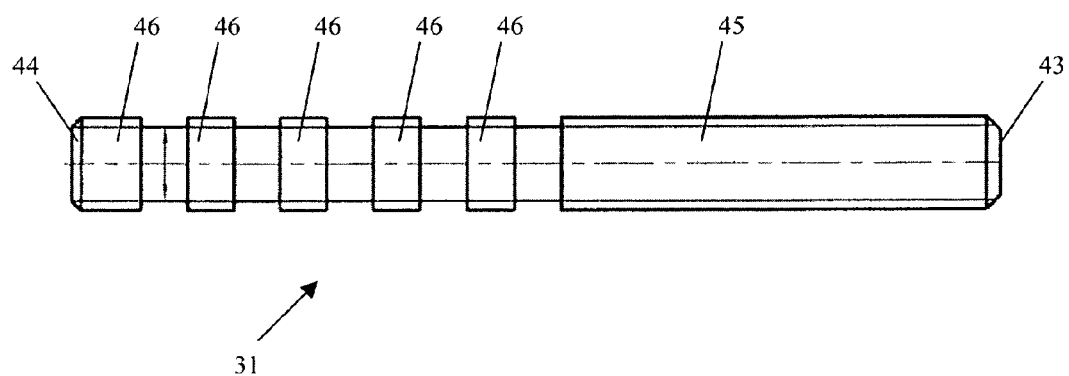
FIG. 4 is a cross-sectional view of a rod, according to an embodiment.

FIG. 4 illustrates an embodiment of the rod 31. The rod comprises a first end 43 and a second end 44. A first threaded section 45 is located at the first end 43. At least a second threaded section 46 is located at the second end 44. In other embodiments, the entire rod is threaded. In the embodiment of FIG. 4, a plurality of spaced threaded sections 46 is provided at the second end 44. This provides for adjustment of the length of the rod. As the bone portion 3 is distracted, the rod will extend above the support 28. When an entire threaded section 46 extends over the surface of the support 28 another threaded section 46 will engage the thread of the swivel device 35 or the threads of the support 28. Hence, the threaded section 46 extending above the support 28 can be cut off or grinded. The diameter of the rod 31 may be about 1.6 mm at the unthreaded section. The threads of the threaded sections 45, 46 may be M2 threads. The length of the rod 31 may be in the range of 15-25 mm, preferably about 20 mm. The length of threaded section 45 may be about 9.5 mm. The length of threaded sections 46 may be about 5 mm. The distance between each threaded section may be about 5 mm.

The support may be a cap splint bar. An interior surface of the cap splint bar has the shape of existing teeth of the patient. Hence, the cap splint bar may be firmly supported by the teeth.

The extension of the cap splint bar may conform to the at least a portion of the dental arch of the patient. In some embodiments, the extension of cap splint bar conforms to the entire dental arch of the patient. The longer the cap splint bar is, the more stable it will be. A cap splint bar provides, thus, for a stable support.

The support provides a fixed point for the entire assembly when it is attached to an adjacent static component, such as neighboring teeth or fixtures in bone not to be distracted. Hence, a fixed point is provided for the device 1, the level adjustment device 23 and the adjustment interface 29.

Figure 5:
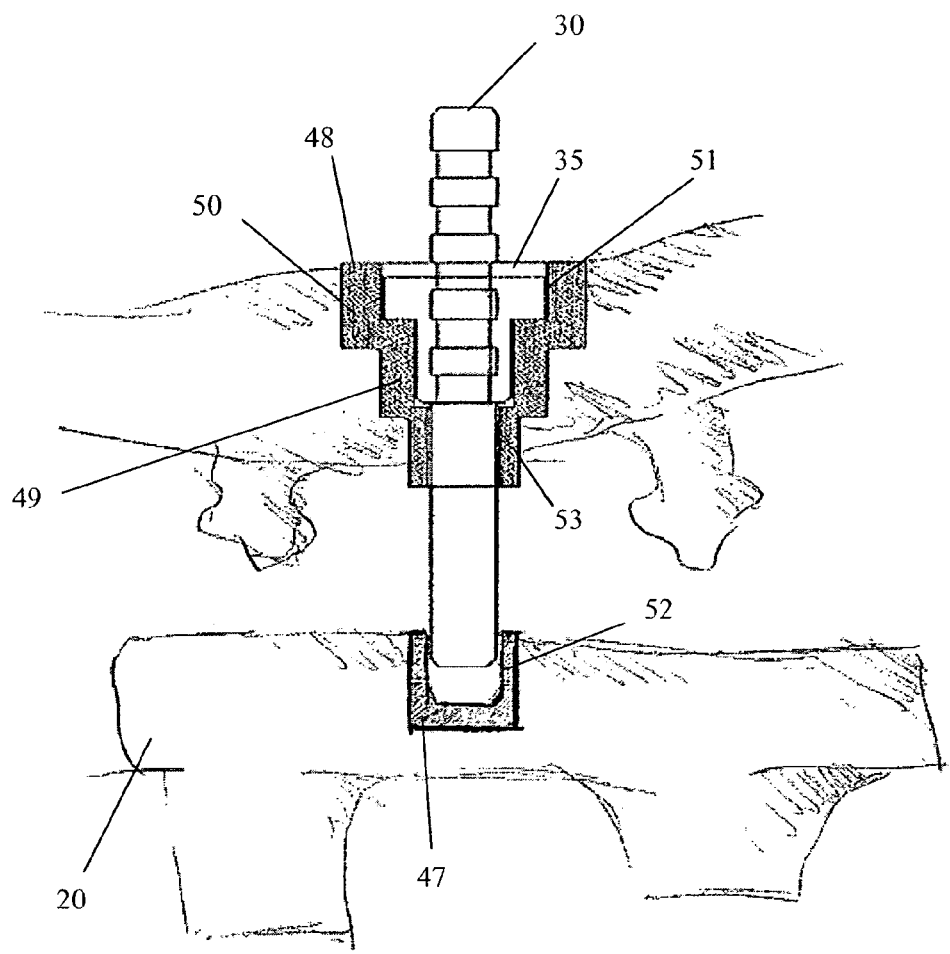
FIG. 5 is a cross sectional view of the rod connected to a first and a second locator, according to an embodiment.

FIG. 5 illustrates a kit of components for forming a device for distracting bone. The kit of components comprises the intermediate member 30, the swivel device 35, a first locator 47, and a second locator 48. The first locator 47 is configured to position the first end of the intermediate member 30 within the bar 20. The second locator 48 is configured to position the seat 34 of the support 28. In some embodiments, the swivel is provided separately from the other components. Instead, a thread is provided in the second locator 48 for temporarily engaging the intermediate member 30 during forming of the device.

Each of the first and the second locator 47, 48 comprises a threaded recess for threadably engaging the threads of the intermediate member 30.

The second locator 48 comprises a first portion 49 with a first diameter and a second portion 50 with a second diameter, which is larger than the first diameter. The second locator comprises a recess 51 having a diameter which corresponds substantially to the diameter(s) of the swivel device 35. A clearance between the swivel device 30 and the recess 51 provides for free rotational movement of the swivel device 35 within the seat 34, which will be formed by the second locator 48, as will be explained below. Hence, the interior surface of the second locator 48 and an exterior surface of the swivel device 35 are at least partly complementary in shape.

The second locator 48 may comprise a third portion 53 having a third diameter, which is smaller than the first diameter of the second locator. The third portion 53 may comprises a through. The third portion provides a lead-through in the bar 20. This provides, e.g., a well-defined lead-though in the bar 20. The third portion can be cut off to a desired length. Hence, this provides for flexibility in shaping the seat, such as making the seat more compact.

The first locator 47 can be shaped as a cap having a threaded recess 52. The exterior surface of the first locator 47 may be cylindrical or flared.

Figure 6A:
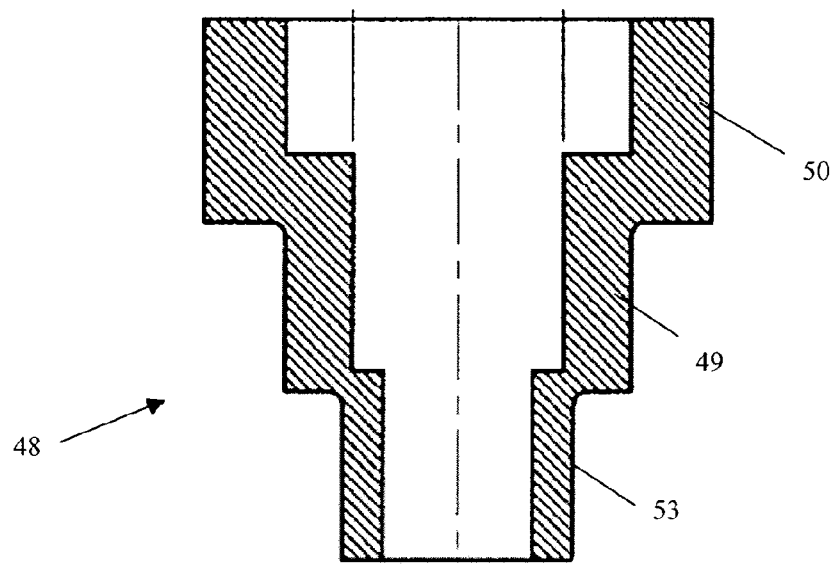
FIG. 6a is a cross sectional view of one of the locators of FIG. 5.
Figure 6B:
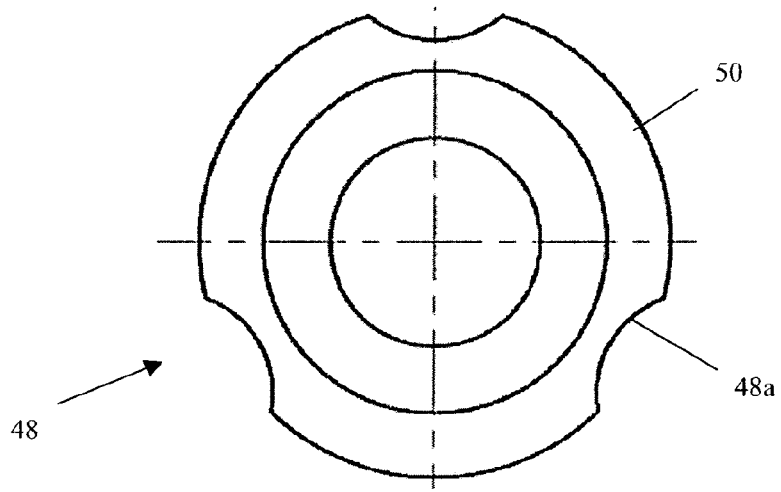

FIGS. 6*a*-6*b* illustrate the second locator 48 in more detail. The diameter of the second portion 50 at its interior surface may be about 3.6-5.4 mm and about 5.6-7.4 mm at its exterior surface. The length of the second portion 50 at its exterior surface may be about 3 mm. The diameter of the first portion 49 at its interior surface may be about 1.6-3.4 mm and about 3.6-5.4 mm at its exterior surface. The length of the first portion 49 at its exterior surface may be about 1.5-33.0 mm. The diameter of the third portion 53 at its interior surface may be about 2.2 mm and about 3.4 mm at its exterior surface. The length of the third portion 53 at its exterior surface may be about 2.5 mm. However, the length of the third portion 53 at its exterior surface may be varied as desired. The above dimensions are only given as examples and should not be construed as limiting.

At least one groove 48*a* may be provided at the exterior surface of the second locator 48. In the embodiment of FIG. 6*a*, the groove 48*a* is a longitudinal groove. Also in this embodiment, the groove 48*a* is located on the second portion 50 of the second locator 48. Here, three grooves 48*a* are provided. The groove 48*a* may provide for improved retention of the second locator 48 and thus a more stable assembly in the end.

FIGS. 7*a*-7*e* illustrates a method for forming a device for distracting bone, or a master thereof, using the kit of components described above. The first locator 47 is provided and connected to the first end 47 of the intermediate member 30. Also, the second locator 48 is provided and connected to the second end of the intermediate member 30.

Figure 7A:
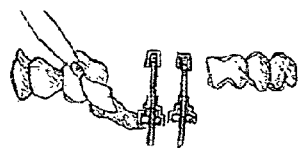
FIGS. 7a-7e are schematic views illustrating a method for forming the device for distracting bone, according to an embodiment.

FIG. 7*a* illustrates forming the support around the second locator 48. The second locator is connected to the second end 44 of the intermediate member 30. In this embodiment, a model, such as a plaster cast, of the patient's teeth is provided. The support 28 is formed around at least a portion, such as the teeth, of the model. Hence a cap splint bar may be provided, which incorporates the second locator 48. If the intermediate member 30 comprises a first and a second rod 31, 32, as described above, the rods 31, 32 may be aligned to be substantially parallel. Both the first portion 49 and the second portion 50 of the second locator 48 can be cast into the support 28. The bar may e.g. be made of metal, such as titanium, a titanium alloy, or Cobalt Chromium (CoCr).

Figure 7B:
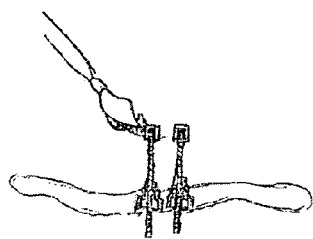

FIG. 7*b* illustrates positioning the first locator 47 within the bar 20, or the master of the bar, of the device 1. This may be provided by forming the bar 20 around the first locator 47. Hence, the first connection interface 21, or a master thereof, will be formed. The first locator 47, such as a first and a second cap, as described above, is connected to the intermediate member 30, such as the first and the second rod 31, 32 described above. Then, the bar 20 is formed around the first locator 47. Furthermore, the bar 20 may be formed around a portion of fixture replicas, such as a connection interface thereof, and possibly also fixture replica screws (not shown), inserted into the model of the patient. Hence, also the first connection interface 21 may be formed. The bar 20 may be formed using conventional dentistry wax for forming masters of dental restorative components, such as a bridges and crowns. Alternatively, the bar is formed directly in metal or another sufficiently strong material.

Figure 7C:
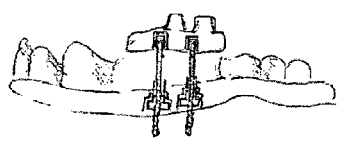

When the shapes of the bridge 20 and the support 28 have been formed around the first and the second locators 47, 48, the components can be detached from the model of the patient for further processing, as is illustrated in FIG. 7*c*.

Figure 7D:
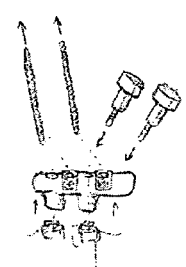
Figure 7E:
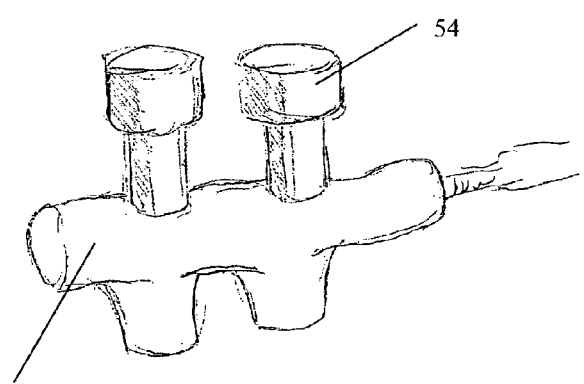

FIGS. 7*d*-7*c* illustrate generating data for manufacturing the bar with the first and the second connection interface 21, 22. The intermediate member 24 is replaced by a third locator 54. Also, the master of the bar is released from the model of the patient, i.e. the fixture replicas. The third locator 54 may be a position locator provided to indicate the position for the engagement part 24, 25. The position locator has a shape which may be known by a processing device ultimately receiving the data. The third locator has a surface mating a surface of the first locator 47. For example, a top surface of the first locator 47 may mate a flange of the third locator 54 when these components are connected. The third locator 54 may have a first and a second cylindrical portion having different diameters. The third locator 54 can have a threaded section with a thread at one end thereof (not shown). The thread of the third locator 54 may be complementary to a thread of the first locator 47. The length of the threaded section of the third locator 47 may be shorter than the length of a threaded section of the first locator 47. Hence, when the third locator 54 is fully seated in the first locator 47, the position, such as orientation in space, of the first locator 47 will be known by knowing the shape of the third locator 54 and how it mates with the first locator 47. This approach may also be used for providing data for the positioning of the first connection interface 21 (not shown).

FIG. 7d illustrates the master of the bar 20 and the first locator 47. At least a portion of the surface of the bar 20 and/or at least a portion of a surface of the third locator 54 can be scanned using a scanner. The scanner may e.g. be a touch probe scanner, such as the Procera Forte® scanner available from the applicant of the present application. Alternatively, the scanner is an optical scanner. The data generated by the scanner can be provided to control a manufacturing machine. The manufacturing machine may e.g. a milling machine. The data can be transmitted to the manufacturing machine. This provides for centralized production, for example via the Procera® system of the applicant of the present inventions. The bar 20 may e.g. be made from metal, such as titanium or a precious metal.

In an alternative embodiment, the master of the bar 20 and the first locator 47 are made in an investment material. A cast may be formed around the master of the bar 20 and the first locator 47. Then, the investment material may be burned off, and the cast filled with the material forming the bar 20. The material may e.g. be metal or a metal alloy, or a ceramic material. The investment material may e.g. be plastic or dentistry wax, or a combination thereof.

The first locator 47 and the second locator 47 may be made of plastic, i.e. an investment material.

Figure 8:
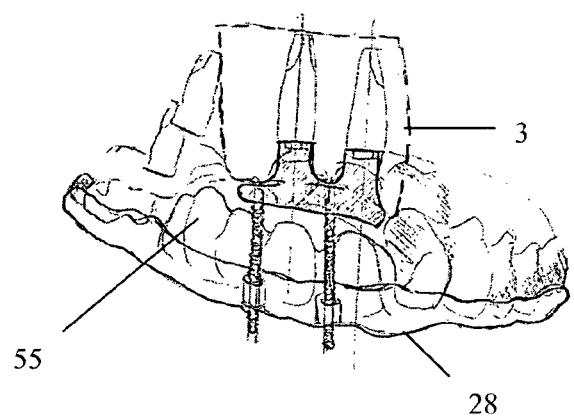
FIG. 8 is a schematic view of the device for distracting bone connected to veneers, according to an embodiment.

FIG. 8 illustrates veneers 55, such as acrylic veneers shaped as teeth, attached to the support 28. The veneers may be attached to the support using a chemical-mechanical bonding agent. When the bone portion 3 is distracted, the veneers can be grinded to conform the contour of the bone portion 3 taking into account any soft tissue lying in between.

The veneers can be provided by prosthetic teeth or temporary veneers. The temporary veneers may be made of acrylic, which is polymerized together with plastic, such as any plastic available for dental purposes. The mixture is then pressure polymerized and adjusted against the frame, in this case the cap splint bar, to which it should be attached. Also, final design adjustment is made. The inside of the cap splint bar may be provided with physical retention elements and recesses. The recesses can be tarnished, e.g. by blasting with aluminum sand, for maximum retention of the veneers.

Figure 9A:
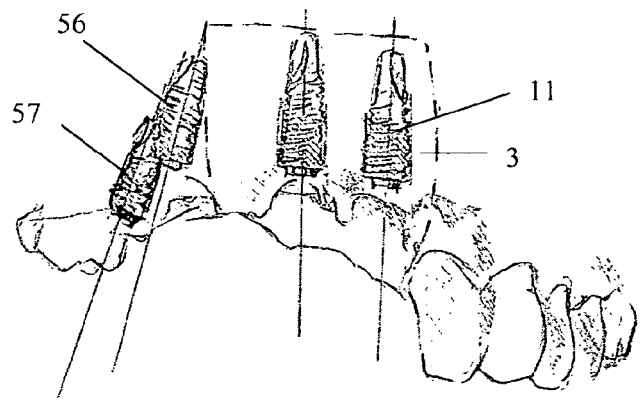
FIGS. 9a-9d are schematic views illustrating distraction of a bone portion, according to an embodiment.
Figure 9B:
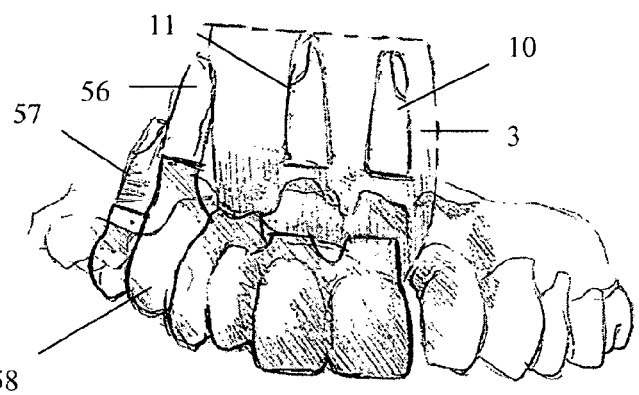

FIGS. 9a-9b illustrates one embodiment of using the inventions. FIG. 9a illustrates the situation before distraction with fixtures 10, 11 in the bone portion 3 to be distracted as well as fixtures 56, 57 in bone not to be distracted.

FIG. 9b illustrates a bridge 58 attached to the fixtures 56, 57 in bone not to be distracted. A distance can be seen between the bridge 58 and the fixtures 10, 11 in the bone portion 3 to be distracted.

Figure 9C:
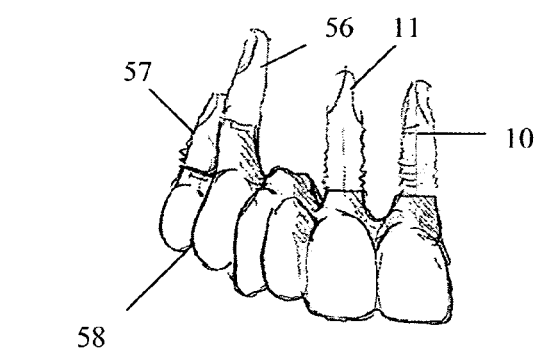

FIG. 9c illustrates the bridge 58 and the planned end location of the bone portion 3 and the fixtures 10, 11 therein.

Figure 9D:
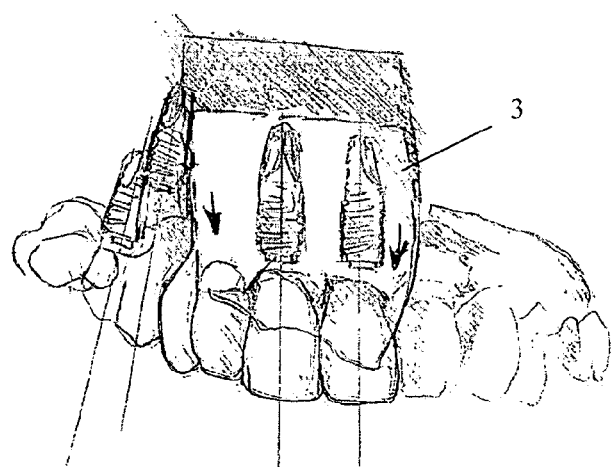

FIG. 9d illustrates distraction of the bone portion 3 including the fixtures 10, 11 therein to the planned location.

Figures 10A, 10B:
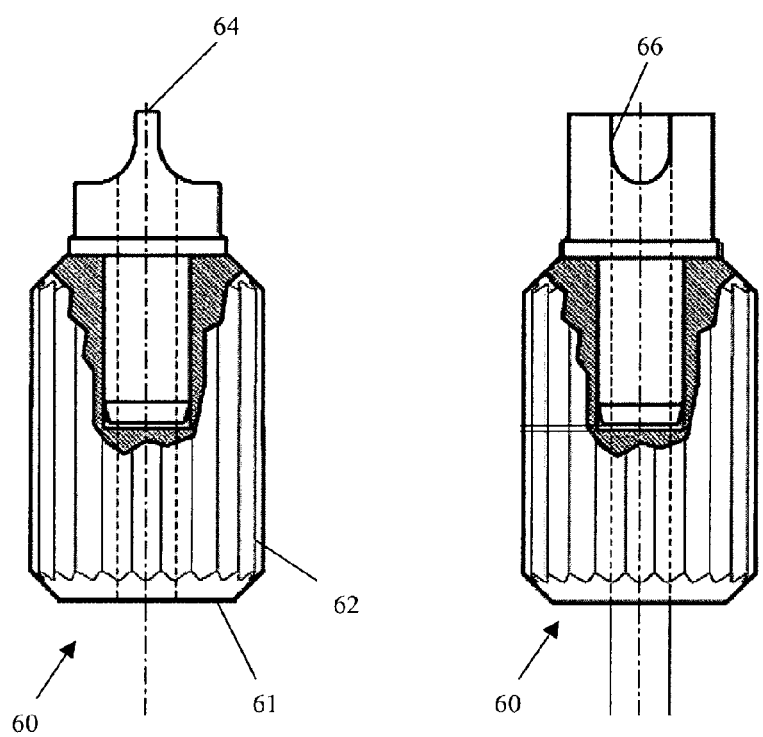
FIGS. 10a-10b are side views of a tool, according to an embodiment.

FIGS. 10a-10b illustrate a tool 60 for rotating the swivel 10. The tool 60 comprises a handle 61. In this embodiment, the handle 61 is substantially cylindrical with a plurality of longitudinal grooves 62. At one end of the handle is provided a protrusion 63. The protrusion has a flat face 64 mating with the groove 41, 42 of the swivel. The flat face 64 has a substantially straight extension with a width. The width of the face is in the range 0.75-0.85 mm. The width of the flat face 64 is in the range of 3.5-6.5 mm. From the flat face 64, the protrusion is arched towards an intermediate cylindrical portion 65 connecting the handle 61 to the flat face. A recess 66 extends from the flat face 64 towards the handle 62. The recess 66 is in this embodiment cylindrical. The diameter of the recess 66 is dimensioned to receive the rod 31, 32. In some embodiments, the diameter of the recess 66 is in the range of 2-3 mm, or slightly more than the diameter of the rod 31, 32. Hence, when the swivel 35 is connected to the rod 31, 32 and rotated clockwise, the rod 31, 32 will extend into the recess 66. Hence, the swivel can be rotated without the rod 31, 32 interfering with the tool 60. The handle 60 may be attached to the intermediate cylindrical portion 65 by a press fit connection.

A marker (not shown) can be provided on the tool 60 to indicate the adjustment in height of the rod 31, 32. The marker may e.g. be positioned on the handle 61 and/or the intermediate cylindrical portion 65. For example, a full turn of the tool could correspond to an adjustment of 0.4 mm in height. Of course, the adjustment in height depends on the pitch of the threads of the rod 31, 32, and the swivel device 35.

FIGS. 11a-11d illustrates different embodiments of the first locator 47.

Figure 11A:
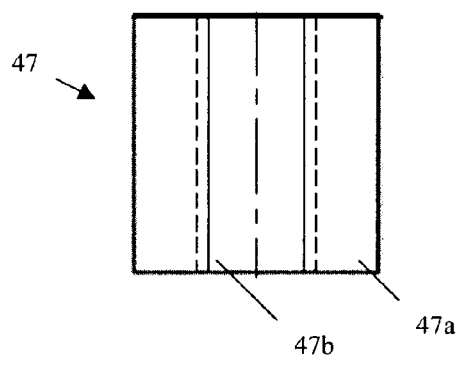
FIGS. 11a and 11c are cross sectional views of embodiments of the first locator.
Figure 11B:
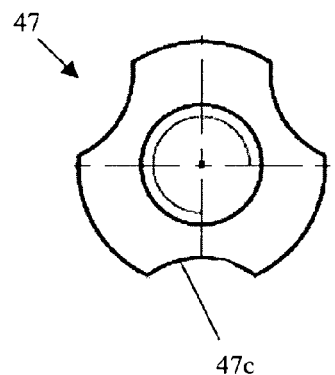
FIGS. 11b and 11d are top views of the locator of FIGS. 11a and 11c, respectively.

FIGS. 11a-11b illustrates an embodiment of the first locator 47 made out of acrylic that can be burned off to provide a cast, as described above. The first locator 47 comprises in this embodiment a generally cylindrical body 47a having a through bore 47b. In this embodiment, the through bore 47b is threaded to mate with a thread of the rod 31, 32. The generally cylindrical body can comprise at least one groove 47c extending in the longitudinal direction of said body 47a. The groove 47c will improve the retention between the exterior surface of the body 47a and any surrounding material. The embodiment of FIG. 11b comprises three such grooves 47c. In combination with this embodiment of the first locator 47 can the second locator 48 described above made of plastic to be burned off be provided.

Figure 11C:
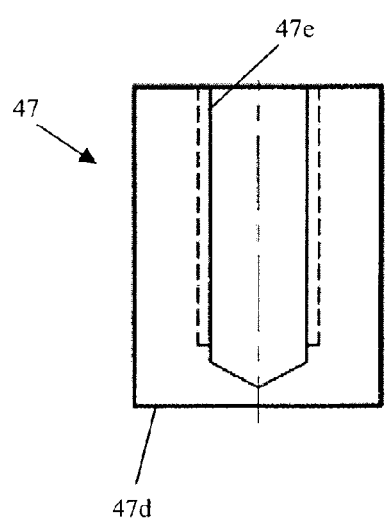
Figure 11D:
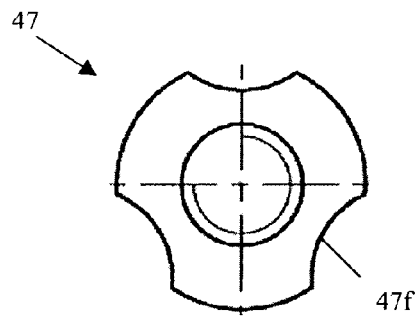

FIGS. 11c-11d illustrate another embodiment of the first locator 47. In this embodiment, the first locator 47 comprises a generally cylindrical body 47d having a blind bore 47e. In this embodiment, the blind bore 47e is threaded to mate with a thread of the rod 31, 32. As in the embodiment of FIG. 11b, the generally cylindrical body 47d comprises a plurality of grooves 47f. The embodiment of FIGS. 11c-11d may be made out of metal, such as titanium. Hence the first locator 47 may be welded into the bar 20. Alternatively, the first locator 47 is made of the material referred to as Non-Ox, which is a precious like metal containing platinum, which increases the melting point above the melting point of many gold compositions at the same time as oxidation is eliminated. Hence the first locator 47 can be welded into a bar 20 made out of a precious metal, such as gold. In combination with this embodiment of the first locator 47 can the second locator 48 be provided by milling in a metal, such as titanium or Non-Ox.

The present inventions have been described above with reference to specific embodiments. However, other embodiments than the above described are equally possible within the scope of the inventions. In addition, while several variations of the inventions have been shown and described in detail, other modifications, which are within the scope of these inventions, will be readily apparent to those of skill in the art based upon this disclosure. It is also contemplated that various combinations or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. For example, different method steps than those described above, performing the method by hardware or software, may be provided within the scope of the inventions. The different features and steps of the inventions may be combined in other combinations than those described.

The invention claimed is:

1. A device for use in distracting a jaw bone of a patient, the device comprising:
   a bar comprising a first connection interface configured for releasable connection of the bar to at least one dental fixture inserted in a bone portion to be distracted; and
   a second connection interface configured to connect the bar to a level adjustment device for distracting the bone portion, wherein the first connection interface comprises a recess or protrusion for interacting with the at least one dental fixture,
   wherein the device further comprises the level adjustment device, which comprises a support configured for attachment to teeth or fixtures in bone not to be distracted, an adjustment interface and an intermediate member, the intermediate member being displaceably connected to the adjustment interface and being displaceable in its axial direction, wherein an interior surface of the support comprises a recess for receiving existing teeth of the patient,
   wherein the bar extends along a first direction and the support extends along a second direction that is generally parallel to the first direction and wherein the intermediate member extends along the axial direction that extends in a third direction that is generally perpendicular to the first and second directions and wherein the recess for receiving existing teeth of the patient of the support extends in the second direction beyond ends of the first connection interface in the first direction.

2. The device according to claim 1, wherein the second connection interface comprises a first engagement part and a second engagement part, which are configured to releasably connect the level adjustment device to the bar, wherein a longitudinal axis of the first engagement part is substantially parallel to a longitudinal axis of the second engagement part.

3. The device according to claim 2, wherein each of the first and the second engagement parts comprises a threaded recess of the bar.

4. The device according to claim 1, wherein the adjustment interface comprises a seat and a swivel device, the swivel device being rotatably arranged in the seat, wherein the intermediate member is displaceably connected to the swivel device.

5. The device according to claim 4, wherein the intermediate member is a rod comprising at least one threaded section located along the length of the rod, the thread of the threaded section being configured to engage a threaded through bore of the swivel device.

6. The device according to claim 5, wherein the rod comprises a plurality of spaced threaded sections.

7. The device according to claim 4, wherein the swivel device comprises at least one flange, and the seat comprises at least one recess, wherein an exterior surface of the swivel device is at least partly complementary in shape to a shape of an interior surface of the recess of the seat.

8. The device according to claim 4, wherein the swivel device comprises a first portion having a first diameter and a second portion having a second diameter, wherein the second diameter is larger than the first diameter.

9. The device according to claim 8, wherein the first and the second portions of the swivel device are cylindrical.

10. The device according to claim 4, wherein the swivel device comprises at least one groove configured to mate with a tool for rotating the swivel device, wherein a plane of the groove extends substantially perpendicularly or substantially in parallel to a longitudinal axis of the intermediate member.

11. The device according to claim 1, wherein the support is a cap splint bar.

12. The device according to claim 1, wherein articulation of the level adjustment device adjust the distance between the bar and the support along the third direction.

13. The device of claim 1, further comprising at least one dental implant configured for implantation into a patient's jawbone and configured to engage the first connection interface of the bar.

14. A method of using a device of claim 1 comprising:
    attaching the bar to the at least one dental fixture;
    attaching the support to said teeth or fixtures in bone not to be distracted; and
    distracting the bone by displacing the intermediate member in its axial direction relative the support.

15. The device of claim 1, wherein the device comprises a first recess and a second recess for receiving existing teeth of the patient and wherein the first recess and the second recess are located beyond ends of the first connection interface in the first direction with the first connection interface being position between the first and second recess.

* * * * *